(12) United States Patent
Bohris

(10) Patent No.: US 7,988,631 B2
(45) Date of Patent: Aug. 2, 2011

(54) SHOCK WAVE THERAPY DEVICE WITH IMAGE PRODUCTION

(75) Inventor: Christian Bohris, Krailling (DE)

(73) Assignee: Dornier MedTech Systems GmbH, Wessling (DE)

( * ) Notice: Subject to any disclaimer, the term of this patent is extended or adjusted under 35 U.S.C. 154(b) by 462 days.

(21) Appl. No.: 11/499,897

(22) Filed: Aug. 4, 2006

(65) Prior Publication Data

US 2007/0055157 A1    Mar. 8, 2007

(30) Foreign Application Priority Data

Aug. 5, 2005  (DE) .................. 10 2005 037 043

(51) Int. Cl.
*A61B 8/00*    (2006.01)
(52) U.S. Cl. ................. 600/439; 601/2; 601/4; 600/459
(58) Field of Classification Search .................. None
See application file for complete search history.

(56) References Cited

U.S. PATENT DOCUMENTS

| | | |
|---|---|---|
| 48,847 A | 7/1865 | Smith |
| 1,750,129 A | 3/1930 | Romine |
| 2,324,702 A | 7/1943 | Hoffmann et al. |
| 2,859,726 A | 11/1958 | Bouyoucos et al. |
| 3,056,312 A | 10/1962 | Timpner et al. |
| 3,249,177 A | 5/1966 | Chelminski |
| 3,505,880 A | 4/1970 | Riordan |
| 3,538,919 A | 11/1970 | Meyer |
| 3,555,880 A | 1/1971 | Menius, Jr. et al. |
| 3,588,801 A | 6/1971 | Leonard |
| 3,618,696 A | 11/1971 | Hurwitz |
| 3,783,403 A | 1/1974 | Hook et al. |
| 3,982,223 A | 9/1976 | Green |
| 3,997,853 A | 12/1976 | Morris et al. |
| 4,189,026 A | 2/1980 | Elliot et al. |
| 4,207,874 A | 6/1980 | Choy |

(Continued)

FOREIGN PATENT DOCUMENTS

DE    1769521    3/1973

(Continued)

OTHER PUBLICATIONS

Bonnefous et al., Time Domain Formulation of Pulse-Doppler Ultrasound and Blood Velocity Estimation by Cross Correlation, *Ultrasonic Imaging*, vol./Iss: 8, pp. 73-85, Date: 1986.

(Continued)

*Primary Examiner* — Unsu Jung
*Assistant Examiner* — Nigel Fontenot
(74) *Attorney, Agent, or Firm* — King & Spalding

(57) ABSTRACT

The invention relates to a shock wave therapy device with a shock wave source for the emission of a shock wave and an ultrasound unit for obtaining image information by means of the emission and reception of ultrasound, whereby the ultrasound unit is provided for the reception of reflected or scattered components of the shock wave for obtaining image information. In addition, the invention relates to a method for obtaining image information for shock wave therapy with the steps: a) emitting ultrasound using an ultrasound unit, b) receiving the reflections of the emitted ultrasound using the ultrasound unit for obtaining image information, c) emitting a shock wave using a shock wave source and d) receiving reflected or scattered components of the shock wave using the ultrasound unit for obtaining image information.

37 Claims, 6 Drawing Sheets

U.S. PATENT DOCUMENTS

| | | | |
|---|---|---|---|
| 4,272,733 | A | 6/1981 | Walling et al. |
| 4,286,168 | A | 8/1981 | Carr |
| 4,286,455 | A | 9/1981 | Ophir et al. |
| 4,336,809 | A | 6/1982 | Clark |
| 4,336,858 | A | 6/1982 | Loyzim |
| 4,398,790 | A | 8/1983 | Righini et al. |
| 4,493,653 | A | 1/1985 | Robbins et al. |
| 4,494,622 | A | 1/1985 | Thompson |
| 4,526,168 | A | 7/1985 | Hassler et al. |
| 4,546,960 | A | 10/1985 | Abrams et al. |
| 4,549,107 | A | 10/1985 | Kaneko et al. |
| 4,580,559 | A | 4/1986 | L'Esperance |
| 4,617,931 | A | 10/1986 | Dory et al. |
| 4,639,923 | A | 1/1987 | Tang et al. |
| 4,641,912 | A | 2/1987 | Goldenberg |
| 4,642,611 | A | 2/1987 | Koerner |
| 4,658,828 | A | 4/1987 | Dory et al. |
| 4,664,111 | A | 5/1987 | Reichenberger |
| 4,669,472 | A | 6/1987 | Eisenmenger |
| 4,672,969 | A | 6/1987 | Dew |
| 4,674,505 | A | 6/1987 | Pauli et al. |
| 4,693,244 | A | 9/1987 | Daikuzono |
| 4,718,421 | A | 1/1988 | Rohwedder et al. |
| 4,721,108 | A | 1/1988 | Heine et al. |
| 4,756,016 | A | 7/1988 | Grady et al. |
| 4,798,196 | A | 1/1989 | Nowacki et al. |
| 4,807,626 | A | 2/1989 | McGirr |
| 4,819,621 | A | 4/1989 | Ueberle et al. |
| 4,829,986 | A | 5/1989 | Eichler et al. |
| 4,962,752 | A | 10/1990 | Reichenberger et al. |
| 4,972,826 | A | 11/1990 | Koehler et al. |
| 5,046,483 | A | 9/1991 | Ogura |
| 5,055,051 | A | 10/1991 | Duncan |
| 5,060,650 | A | 10/1991 | Wurster et al. |
| 5,067,493 | A | 11/1991 | Inbar et al. |
| 5,070,861 | A | 12/1991 | Einars et al. |
| 5,072,722 | A * | 12/1991 | Granz ................. 601/4 |
| 5,072,723 | A | 12/1991 | Viebach |
| 5,072,960 | A | 12/1991 | Sperko |
| 5,090,401 | A | 2/1992 | Schwieker |
| 5,143,073 | A | 9/1992 | Dory |
| 5,144,953 | A | 9/1992 | Wurster et al. |
| 5,149,030 | A | 9/1992 | Cockrill |
| 5,165,412 | A * | 11/1992 | Okazaki ................. 600/439 |
| 5,191,560 | A | 3/1993 | Lobentanzer et al. |
| 5,209,221 | A | 5/1993 | Riedlinger |
| 5,209,222 | A | 5/1993 | Vibach et al. |
| 5,243,985 | A | 9/1993 | Aida et al. |
| 5,269,306 | A | 12/1993 | Warnking et al. |
| 5,285,772 | A | 2/1994 | Rattner |
| 5,287,856 | A | 2/1994 | Treiber |
| 5,289,856 | A | 3/1994 | Strock et al. |
| 5,301,659 | A | 4/1994 | Brisson et al. |
| 5,358,466 | A | 10/1994 | Aida et al. |
| 5,394,786 | A | 3/1995 | Gettle et al. |
| 5,409,002 | A | 4/1995 | Pell |
| 5,435,311 | A | 7/1995 | Umemura |
| 5,450,848 | A * | 9/1995 | Okazaki et al. ............. 600/439 |
| 5,572,569 | A | 11/1996 | Benoit et al. |
| 5,582,578 | A | 12/1996 | Zhong et al. |
| 5,642,898 | A | 7/1997 | Wise |
| 5,658,239 | A | 8/1997 | Dekmenico |
| 5,769,790 | A | 6/1998 | Watkins et al. |
| 5,795,311 | A | 8/1998 | Wess |
| 5,800,365 | A | 9/1998 | Zhong et al. |
| 5,810,748 | A | 9/1998 | Ueberle |
| 5,836,898 | A | 11/1998 | Schwieker |
| 5,864,517 | A | 1/1999 | Hinkey et al. |
| 6,036,611 | A | 3/2000 | Bigo et al. |
| 6,036,661 | A | 3/2000 | Schwarze et al. |
| 6,119,034 | A | 9/2000 | Herrmann et al. |
| 6,135,357 | A | 10/2000 | Herrin et al. |
| 3,556,928 | A | 1/2001 | Zolg |
| 6,276,471 | B1 | 8/2001 | Kratzenberg et al. |
| 6,298,264 | B1 | 10/2001 | Zhong et al. |
| 6,386,560 | B2 | 5/2002 | Calender |
| 6,408,614 | B1 | 6/2002 | Eizenhofer |
| 6,508,774 | B1 * | 1/2003 | Acker et al. ............. 601/2 |
| 6,618,206 | B2 | 9/2003 | Tarakci et al. |
| 6,875,176 | B2 | 4/2005 | Mourad et al. |
| 6,915,697 | B2 | 7/2005 | Eizenhofer |
| 6,926,680 | B2 | 8/2005 | Eizenhofer |
| 7,610,079 | B2 * | 10/2009 | Schwarze et al. ............. 600/427 |
| 2001/0048732 | A1 | 12/2001 | Wilson et al. |
| 2002/0095087 | A1 | 7/2002 | Mourad et al. |
| 2002/0125664 | A1 | 9/2002 | Eriksson et al. |
| 2003/0078523 | A1 | 4/2003 | Burkhardt et al. |
| 2003/0130649 | A1 | 7/2003 | Murray et al. |
| 2003/0135205 | A1 | 7/2003 | Davenport et al. |
| 2004/0059319 | A1 * | 3/2004 | Bohris ............. 606/2.5 |
| 2005/0010140 | A1 | 1/2005 | Forssmann |
| 2006/0184075 | A1 * | 8/2006 | Restle et al. ............. 601/2 |
| 2007/0055157 | A1 | 3/2007 | Bohris |
| 2007/0219601 | A1 | 9/2007 | Neuberger |
| 2008/0200813 | A1 * | 8/2008 | Quistgaard ............. 600/459 |
| 2008/0267927 | A1 | 10/2008 | Lutz et al. |

FOREIGN PATENT DOCUMENTS

| | | |
|---|---|---|
| DE | 3723815 | 3/1973 |
| DE | 3119295 | 12/1982 |
| DE | 3328039 | 2/1985 |
| DE | 3617032 | 1/1987 |
| DE | 3723815 | 6/1988 |
| DE | 3921808 | 6/1988 |
| DE | 3703335 | 8/1988 |
| DE | 3703338 | 8/1988 |
| DE | 3916093 | 11/1990 |
| DE | 3921808 | 1/1991 |
| DE | 4113697 | 1/1991 |
| DE | 9102394.7 | 6/1991 |
| DE | 4125950 | 11/1992 |
| DE | 9414692 | 9/1994 |
| DE | 4318237 | 12/1994 |
| DE | 4443495 | 6/1996 |
| DE | 4446192 | 7/1996 |
| DE | 19509004 | 10/1996 |
| DE | 4205030 | 4/1997 |
| DE | 29712035 | 10/1997 |
| DE | 69219342 | 11/1997 |
| DE | 19625164 | 1/1998 |
| DE | 19631246 | 2/1998 |
| DE | 19702829 | 7/1998 |
| DE | 19843680 | 9/1998 |
| DE | 20315924 | 9/1998 |
| DE | 19718511 | 7/1999 |
| DE | 10111800 | 3/2001 |
| DE | 10206193 | 7/2003 |
| DE | 03-08-1973 | 7/2007 |
| DE | 102006037289 | 2/2008 |
| EP | 0139823 | 5/1985 |
| EP | 370336 | 8/1988 |
| EP | 369177 | 5/1990 |
| EP | 0369177 | 5/1990 |
| EP | 0445322 B1 | 9/1991 |
| EP | 0300315 B1 | 4/1992 |
| EP | 526758 | 2/1993 |
| EP | 0548048 B1 | 6/1993 |
| EP | 4302537 | 4/1994 |
| EP | 0367116 B1 | 6/1994 |
| EP | 0460536 | 10/1994 |
| EP | 511506 | 10/1996 |
| EP | 715831 | 2/1999 |
| EP | 1749488 | 2/2007 |
| GB | 0002799 A | 3/2000 |
| JP | 02-215451 | 8/1990 |
| RU | 402070 | 4/1974 |
| WO | WO 86/06269 A1 | 11/1986 |
| WO | WO 88/03782 A1 | 6/1988 |
| WO | WO 96/34567 A1 | 11/1996 |
| WO | WO 0013598 | 3/2000 |
| WO | WO 00/25125 A1 | 5/2000 |
| WO | WO 00/53263 A1 | 9/2000 |
| WO | WO 01/30281 A1 | 5/2001 |
| WO | WO 2007/064783 | 6/2007 |

OTHER PUBLICATIONS

Foster et al., Flow Velocity Profile via Time-Domain Correlation: Error Analysis and Computer Simulation, *IEEE Transactions on Ultrasonics Ferroelectrics and Frequency Control*, vol./Iss: 37(2), pp. 164-175, Date: May 1990.

Hubert et al., Influence Wave Pressure Amplitude and Pulse Repetition Frequency on the Lifespan, Size and Number of Transient Cavities in the Field of an Electromagnetic Lithotripter, *Physics in Medicine and Biology*, vol./Iss: 43, pp. 3113-3128, Date: 1998.

Madsen et al., An Anthropomorphic Torso Section Phantom for Ultrasonongraphy, *Medical Physics*, vol./Iss: 7 (1) pp. 43-50, Date: Jan./Feb. 1980.

Paterson et al., Slowing the Pulse Repetition Frequency in Shock Wave Lithotripsy (SWL) Improves Fragmentation in Vivo, pp. 1-2, Date: 2001.

Paterson et al., Stone Fragmentation during Shock Wave Lithotripsy Is Improved by Slowing the Shock Wave Rate: Studies with a New Animal Model, *The Journal of Urology*, vol./Iss: 168 pp. 2211-2215, Date: Nov. 2002.

Paterson, R. et al., An in Vivo Test of Shock Wave Rate Effect on Stone Fragmentation in SWL , *The Journal of Urology*, vol./Iss: 165 (5)Sup. 1540, Date: Jun. 6, 2001.

Wiksell et al., Implications of Cavitation Phenomena for Shot Intervals in Extracorporeal Shock Wave Lithotripsy, *British Journal of Urology*, vol./Iss: 75, pp. 720-723, Date: 1995.

Wu et al., Application of Hydroelastic Waves to Removal of Small Gallstones, *Journal of Biomechanical Engineering*, vol./Iss: 103, pp. 79-82, Date: May 1981.

Bohris et al., "Hit/Miss Monitoring of ESWL by Spectral Doppler Ultrasound", *Ultrasound in Med. And Biology*, vol. 29; pp. 705-712, 2003.

Chen, W., "A Light-Scattering Technique for Investigating the Destruction of Ultrasound Contrast Agents," *IEEE Ultrasonics Symposium*, pp. 1683-1686, 2001.

Coleman et al., "A survey of the Acoustic Output of Commercial Extracorporal Shock Wave Lithrotripters," *Ultrasound in Med. And Biology*, vol. 15, pp. 213-227, 1989.

Seitz, M., "Der Dioden Laser, Ex Vivo-Untersuchungen zu den Vaporisations -und Koasgulationseigenschalten," *Uroge A*, vol. 46(9), 1242-1247, 2007.

Wenst-Nordahl, G., "980-nm Diode laser: ANovel Laser Technology for Vaporization of the Prostrate, " *Eur Urol*, vol. 52, pp. 1723-1728, 2007.

Zhou et al., "Measurement of High Intensity Focused Ultrsound Fields by a Fibre Optyic Probe Hydrophone, " *J. Acoust. Soc. Am.*, vol. 120, pp. 676-685, 2006.

Bachmann et al., "ESWT and Ultrasound Imaging of the Musculoskeletal System", $2^{nd}$ revised and translated edition, Steinkopff Darmstadt. pp. 4-20, 1999.

\* cited by examiner

SHOCK WAVE THERAPY DEVICE WITH IMAGE PRODUCTION

RELATED APPLICATION

This application claims priority under 35 U.S.C. §119 (a) to German Patent Application No. 102005037043.8, filed on Aug. 5, 2005, which is incorporated herein by reference.

FIELD OF THE INVENTION

The invention relates to a shock wave therapy device with a shock wave source for the emission of a shock wave and an ultrasound unit for image production by means of emission and reception of ultrasound. Furthermore, the invention relates to a method of producing image information for shock wave therapy.

BACKGROUND OF THE INVENTION

In shock wave therapy, kidney or gall stones (concrements) are disintegrated by means of focused shock waves. Other forms of shock wave therapy are used for the treatment of pain, the treatment of closed vessels, the treatment of the cardiac muscle, in a corresponding target area. The shock wave source generally has a focus which is determined by its geometry. For example, the focus can be generated through a lens.

In order to direct the focus of the shock wave source at the concrement or target area, it is necessary to locate the concrement or corresponding structures of the target area. Location information using both X-rays and ultrasound is known.

For example, German Patent DE 203 15 924 U1 discloses a shock wave source that is known where an ultrasound converter is connected with the shock wave source in a specified geometric arrangement, so that the concrement can be located with the ultrasound converter. Because of the fixed geometric relationship, the position of the focus can be indicated by a marker, such as a cross, in the ultrasound image. Therefore, during image monitoring, the concrement or target area can be moved in relation to the focus until alignment is achieved.

However, in German Patent DE 203 15 924 U1, the physical shock wave focus is not proven and displayed using measurement technology. Therefore, incorrect adjustment of the mechanical coupling of the shock wave source can cause deviations between the displayed and actual focus positions. This incorrect adjustment would lead to ineffective treatment with an increased risk of side effects. In addition, it cannot be directly detected whether the shock wave is reaching the focus to a sufficient degree. Faulty acoustic coupling between the shock wave and the body to be treated can weaken the shock wave energy applied. Furthermore, faulty acoustic coupling can occur between the shock wave and strong reflections on, for example, ribs located above the target organ.

It is known from German patent DE 37 03 335 C2 that an ultrasound receiver unit in the form of a PVDF foil can be provided. This ultrasound receiver unit can receive a reflected echo which occurs at a concrement when the shock wave pulse hits the concrement. The disadvantage of this is that image production is only possible with application of a shock wave pulse, but not beforehand, to allow the shock wave source to be adjusted. Furthermore, this method requires a shock wave therapy device to meet certain structural preconditions, such as the existence of a lens.

European patent EP 0 460 536 A1 describes a lithotripter in which no imaging is used to align the focus and the concrement. Instead, a piezoelectric shock wave source is used to generate a weak ultrasound pulse and the echo is received on a time-resolved basis, so that it can be concluded from a strong echo that the position of the focus coincides with the concrement. The disadvantage of this method is that no direct image production is possible, although this is a major advantage for carrying out lithotripsy, since direct image production can be used to determine the shape, size and state of disintegration of the concrement. In addition, presenting the surrounding anatomy is important for safe treatment, since the target can only be clearly identified in this way, and adjacent risk structures can be protected.

Furthermore, an alignment of a B image with a speed image is known from German patent DE 4113697 A1. Movements of the concrement, for example, or cavitation blistering triggered by the shock wave can be detected in this way. However, the disadvantage is that movements only occur in the case of cavitations which are, in themselves, unwanted, or only when the concrement is hit by the shock wave. Otherwise, no movements can be detected and the method is no longer helpful.

SUMMARY OF THE INVENTION

The object of the present invention is to provide a shock wave therapy device and a method with which the position of the focus and the concrement or the target area can be monitored as cost-effectively as possible and in a way that is as least susceptible to errors as possible. This object is solved by a shock wave therapy device according to the claims herein.

The shock wave therapy device also uses the same ultrasound unit that is used for normal image production to register components of the shock wave for obtaining image information which are reflected or scattered in the focus area of the shock wave. Therefore, it is possible to obtain an image of the shock wave focus itself. Because this shock wave focus is received with the same ultrasound unit as the normal image, optimum monitoring of the treatment is possible. The shock wave focus can be aligned with the target area or concrement without any doubt. Detection of the shock wave focus ensures that the acoustic energy of the therapy wave reaches the target.

The ultrasound unit comprises preferably an electrical transducer such as a piezoelectric transducer which can be electronically focused. This is made up of a large number of individual elements which are arranged as either a 1-dim or 2-dim array. This type of transducer allows a high-quality ultrasound image to be obtained in a way that is cost-effective.

The ultrasound unit can also comprise two or more piezoelectric transducers which have different frequency characteristics. Each transducer, in turn, can be built up from a number of transducer elements. Therefore, it is possible to use one transducer for normal ultrasound image production and the other for receiving components of the reflected shock wave for obtaining image information. The two transducers are grouped together in one ultrasound unit, so that their position in relation to each other is known.

The ultrasound unit can also comprise transducers which are made up of transducer elements with different properties. For example, two or more different types of transducer elements which each have different frequency characteristics. Furthermore, the various transducer elements can always be arranged alternately. This applies for both 1-dimensional arrangements and 2-dimensional arrays.

The various ultrasound units mentioned can be linked with an electronic signal processing device which can carry out both radiation focusing and reception focusing. In radiation focusing, the individual elements of the ultrasound unit are activated after a time delay, producing an outgoing wave that is focused. Similarly, with reception focusing, the received signals can be assigned a time delay electronically, so that the reception of ultrasound from a particular area (focus of reception focusing) is particularly intensive. In this way, scanning by line is possible both by emission focusing and by reception focusing or both at the same time. Emission focusing is not used to display the shock wave because the shock wave is generated by the shock wave source rather than by the transducer itself. However, the reception focusing can be used to show the echoes generated by the shock wave on a location resolved basis.

Advantageously, the shock wave therapy device is built in such a way that the image signal production by means of the emission and reception of ultrasound can take place at different times from the image signal production through the reception of the reflected and scattered parts of the shock wave. This means that electronic signal processing of the different signals is possible in each case.

For the operating staff, it is an advantage if the different image information obtained is overlapped or superimposed so that it is shown in a single image. In this way, it is, in particular, easily possible to achieve alignment of the shock wave focus with the concrement.

Piezoelectric (see German Patent DE 3119 295 A1), electromagnetic (see German Patent DE 37 03 338A1) and electrohydraulic (see German Patent DE 36 17 032) shock wave sources are known, each of which can also be used in the present invention. The various designs may show more or less marked imprecisions at the time when the shock wave is triggered. For example, with the electrohydraulic shock wave source the precise time depends on the degree of contact erosion of the electrodes.

Advantageously, a corresponding sensor is therefore provided with which the precise time of the shock wave source emission can be determined so that the electronics of the ultrasound unit can switch over accordingly to the reception of reflected or scattered components of the shock wave. Therefore, it is possible to achieve the most complete flow of image production possible, i.e. to ensure that image information can be obtained immediately before the emission of the shock wave by means of emission and reception of the ultrasound by the ultrasound unit.

In the case of shock wave sources where the timing of the shock wave is known precisely because it is triggered by a corresponding (e.g. electrical) signal, there can also be a direct coupling between the signal triggering for the shock wave source and the corresponding operation of the ultrasound unit for the corresponding production of images by components of the shock wave.

The piezoelectric crystals of the electronic transducers should have a receiver area that is as broadband as possible, since then both the reception for the B image and the reception for the display of the shock wave can be optimized. For the B imaging, depending on the depth of the image area, frequencies between 2 and 8 MHz are suitable. The shock wave frequently has a very wide frequency spectrum which depends on the type of shock wave generation and the height of the shock wave pressure amplitude. As a rule, the maximum of the frequency spectrum is below 1 MHz. However, particularly in the shock wave focus, where non-linear effects occur because of the high pressure amplitudes, many high-frequency components are found in the range of 3 to 5 MHz, which can be used for image production. By using a broadband transducer, it is possible to select the best frequency for the image area in each case, depending on the application. These may also be different frequencies for the two different types of image information. The choice can be made by acoustic or electronic signal filtering.

Transducers or transducer elements with various frequency characteristics may also be provided. For example, transducers or transducer elements with a good reception sensitivity below 1 MHz (reception sensitivity maximum below 1 MHz) may be provided, plus other transducers or transducer elements with a good reception sensitivity above 1 MHz, such as 2, 3, 4, 5, 6, 7, 8, 9 or 10 MHz. Instead of a good reception sensitivity below or above 1 MHz, the good reception sensitivity can also be below or above 0.5, 1.5, 2, 2.5, 3, 3.5, 4, 4.5, 5, 6, 7, 8, 9, 9.5 or 10 MHz or in between, depending on the various requirements. The one type of transducer or transducer elements are optimized for image production with shock waves and the others for normal B image production.

In the method for obtaining image information, for producing a B image, for example, an ultrasound is emitted by an ultrasound unit and then received. Furthermore, a shock wave is emitted using a shock wave source and the reflected or scattered components of the shock wave are received with the ultrasound unit, so that image information can be obtained.

Advantageously, the shock wave source can emit shock waves with different intensities. For adjustment purposes, for example, a shock wave can be emitted with a lower intensity than a shock wave that is intended for disintegrating stones. The intensity of the shock wave for adjusting only needs to be large enough for it to be possible for the reflected and scattered components of the shock wave to be received with the ultrasound unit.

BRIEF DESCRIPTION OF THE DRAWINGS

An embodiment of the shock wave therapy device and the method will be explained using the Figures.

DETAILED DESCRIPTION OF EXEMPLARY EMBODIMENTS

Figure 1:
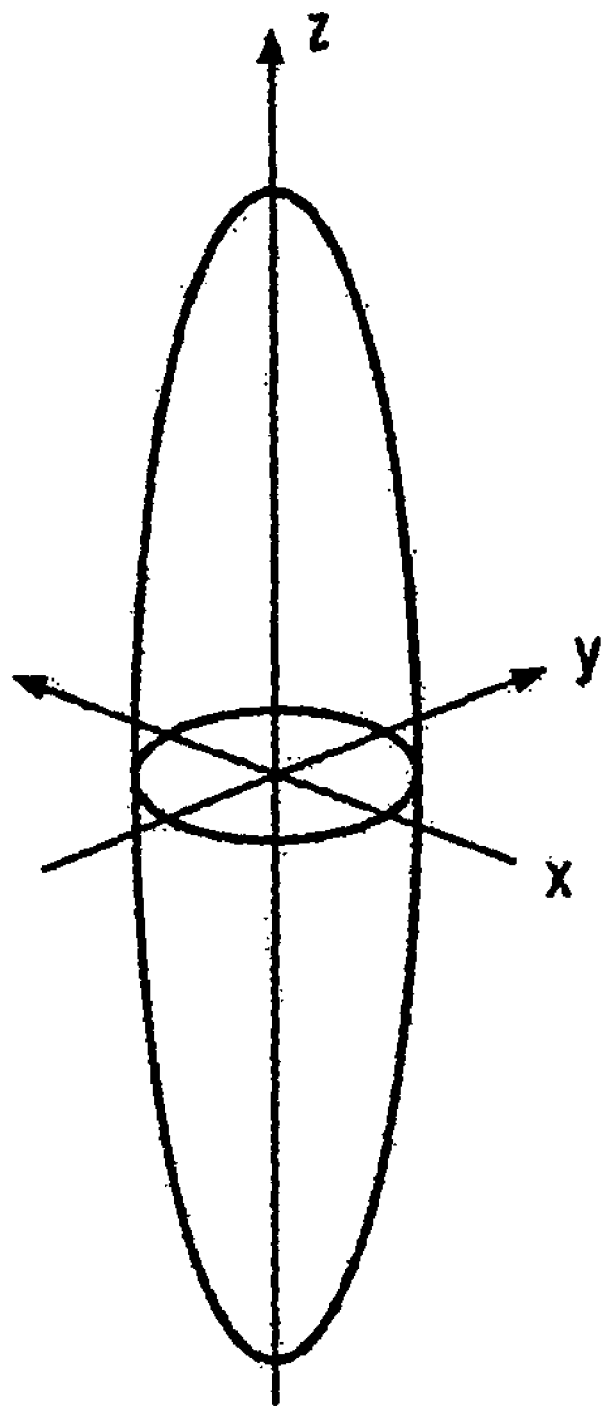
FIG. 1 shows a schematic diagram of the shock wave focus.

Referring to the drawings, in which like numerals represent like elements, aspects of the exemplary embodiments will be described herein below.

FIG. 1 shows the ellipsoidal isobars of a shock wave focus, for example, the −6 dB isobars relating to the focus tip value, which may be around 3 to 10 cm long in the Z direction and which is typically 2 to 15 mm wide in the X and Y direction.

The following description describes a lithotripter as an example of a shock wave therapy device. For the other treatment devices used in the treatment of pain, etc. (see above), the embodiments apply accordingly.

Figure 2:
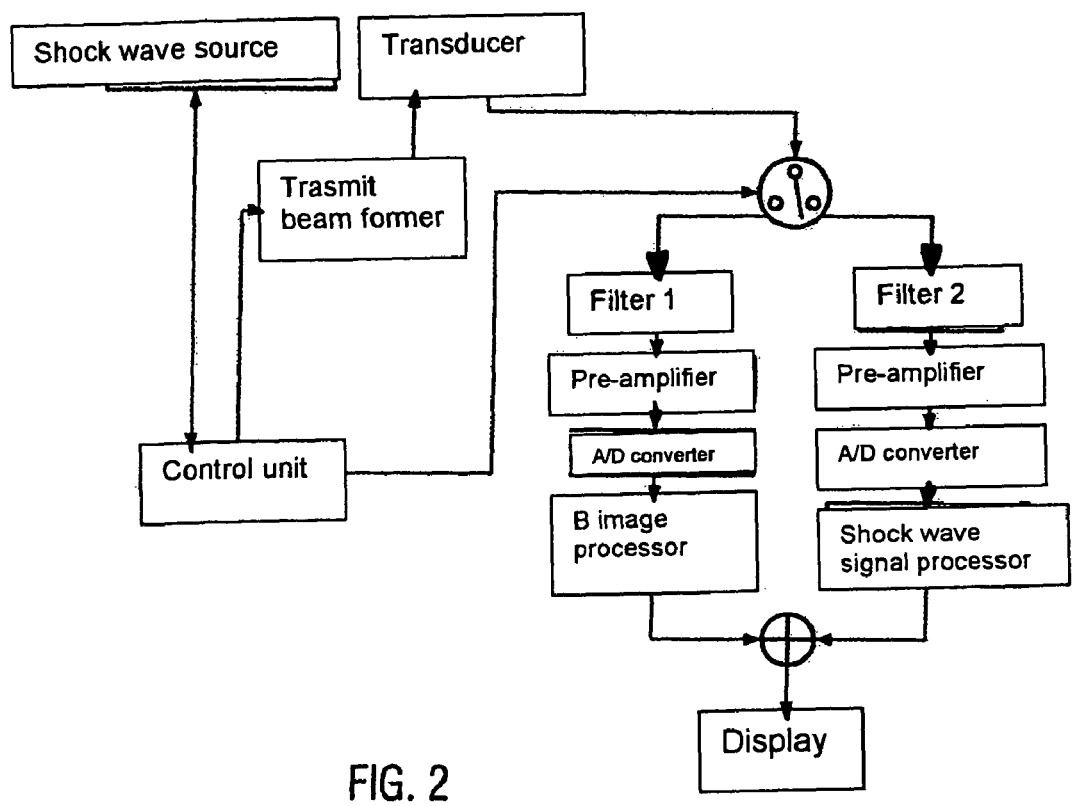
FIG. 2 shows a schematic diagram of the various elements in the shock wave therapy device.

FIG. 2 shows the various elements of the lithotripter diagrammatically. The lithotripter comprises a shock wave source and a transducer which is used here as an ultrasound unit. The ultrasound unit can be positioned on or next to the symmetry axis of the shock wave source (see FIGS. 3 and 4). For example, the ultrasound unit can be a linear arrangement of 128 individual piezoelectric elements. More or fewer elements can be provided, such as 30, 40, 50, 60, 70, 80, 90, 100, 110, 120, 130, 140, 150, 160, 170, 180, 190 or 200 or more.

The shock wave source is preferably electromagnetic.

A control unit is used to control the shock wave source so that a shock wave can be emitted at controlled times. Furthermore, the control unit controls a beam former for emitting ultrasound ("transmit beam former"). This controls the transducer in such a way that, for example, by means of emission focusing, ultrasound pulses are emitted for obtaining image information on particular image lines. With emission focusing, the individual transducer elements are controlled with such a time lag that the individual transmitted ultrasound waves—also known as Huygens' individual waves—superimpose structurally at the focus point. As a rule, the individual channels are also weighted with an apodisation function in order to suppress secondary maxima. The emitted ultrasound pulse is scattered and reflected in the body. The transducer elements receive these reflections as analog electrical signals. These are taken to a normal B image processor. The normal B image processor can be used to produce standard ultrasound images, which can be shown on a display.

If a shock wave is emitted, the emission of ultrasound pulses by the transducer can be interrupted. However, the transducer elements continue to be used for reception. The signals resulting from the shock wave echoes are forwarded to a shock wave signal processor for image production. The short-term cessation of the emission of ultrasound pulses and the forwarding of the signals as required to the B image processor or shock wave signal processor is controlled by the control unit.

Depending on the further processing by the B image processor or by the shock wave signal processor, the signal is filtered, amplified and digitized accordingly. The separated filtering and pre-amplification allows signal treatment that is suitably modified. If, for example, the intensity of the two signals is clearly different, this can be balanced out by pre-amplification that vanes in strength accordingly. For example, the filtering can limit the signal to the frequency range that is relevant in each case, in order to reduce noise.

The shock wave signal processor calculates the shock wave pattern. The calculation is essentially based on the reception focusing as used basically in the case of normal B image production too.

Figure 3:
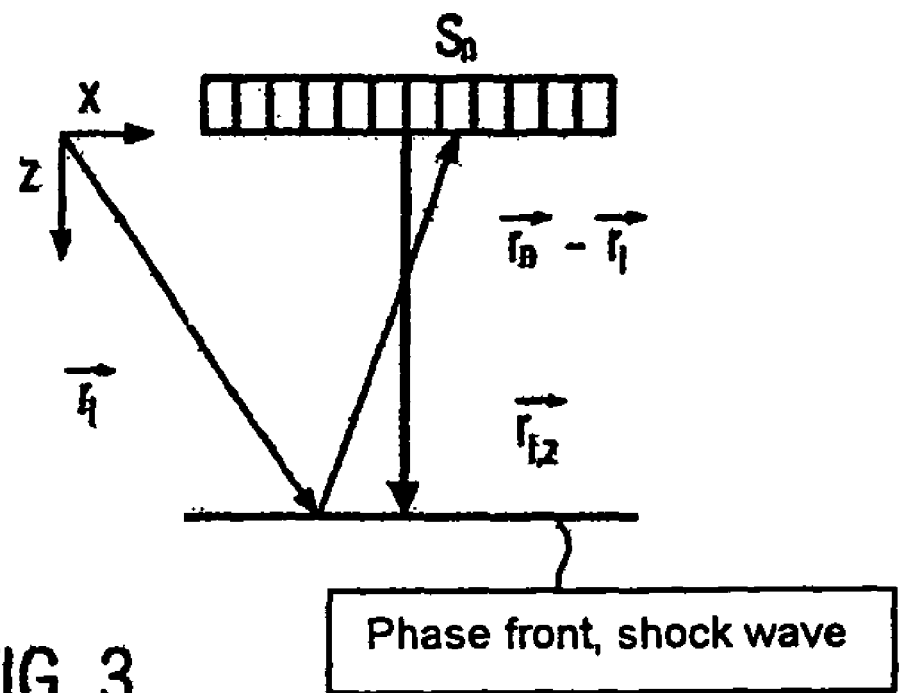
FIG. 3 shows the locational relationship between the direction of spread of the shock wave, the transducer and the image point if the ultrasound unit is centrally positioned.

FIG. 3 shows the geometry for when the transducer is positioned centrally in relation to the shock wave source.

Let the axial axis of the shock wave source and of the transducer—without limitation of the generality—be the Z axis. Let the position of the transducer elements be $\vec{r}_n$. In order to determine the signal at an image point $\vec{r}_1$, the individual signals $S_n$, which are picked up at the transducer elements n, are added, whereby the individual signals are phase-delayed in relation to each other.

The phase delays should be chosen in such a way that they balance out the relative path differences of $\vec{r}_1$ (location of reflection or scatter) to the various $\vec{r}_n$, (receivers). The signal intensity S for the location $\vec{r}_1$ can be calculated according to $$S(\vec{r}_1) = \sum_{n=1}^{N} Apod_n(\vec{r}_1) \cdot S_n\left(\frac{r_{1,z} + |\vec{r}_n - \vec{r}_1|}{c}\right) \quad \text{(Equation 1)}$$

in which $Apod_n(\vec{r}_1)$ is the apodisation function, $S_n$, the time dependency of the intensity measured at the location $\vec{r}_n$ and c the speed of the spread of sound.

The apodisation function $Apod_n(\vec{r}_1)$ serves to suppress secondary maxima and corresponds to the apodisations as used in conventional B image production.

In equation 1, it was assumed, through the consideration of $r_{1,z}$, that the shock wave has an even phase front. This is actually only precisely true in the lateral plane of the shock wave focus.

Figure 4:
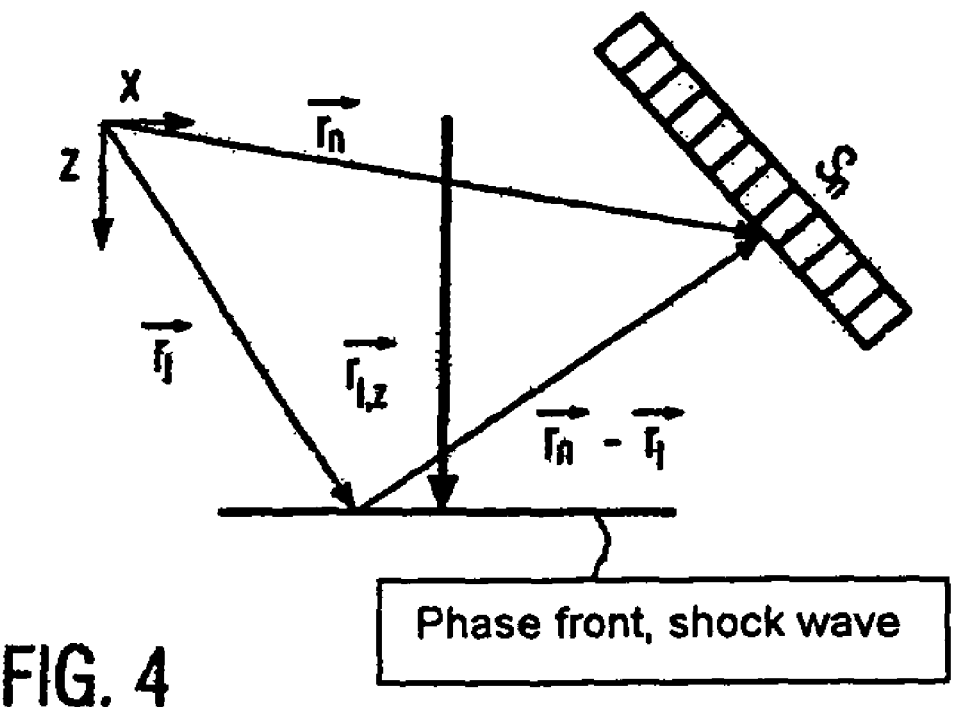
FIG. 4 shows the locational relationship between the direction of spread of the shock wave, the transducer and the image point if the ultrasound unit is not centrally positioned, whereby the axial axis of the shock wave source and the ultrasound image plane are in a single plane.

However, equation 1 represents a sufficiently precise approximation for the particularly interesting areas, such as the focus area, and on and near to the axial axis. In principle, the running time of the phase front can also be indicated for any point $r_1$ and an exact solution can be calculated. If the transducer and shock wave axis are not parallel, but are at an angle as shown in FIG. 4, equation 1 applies similarly.

The calculation of a shock wave pattern requires extensive calculation work. However, because the shock wave rate in lithotripsy typically does not exceed 2 Hz, a pattern can actually be calculated economically today. Similarly, as with conventional B imaging, rapid approximation solutions can also be realized.

Figure 5:
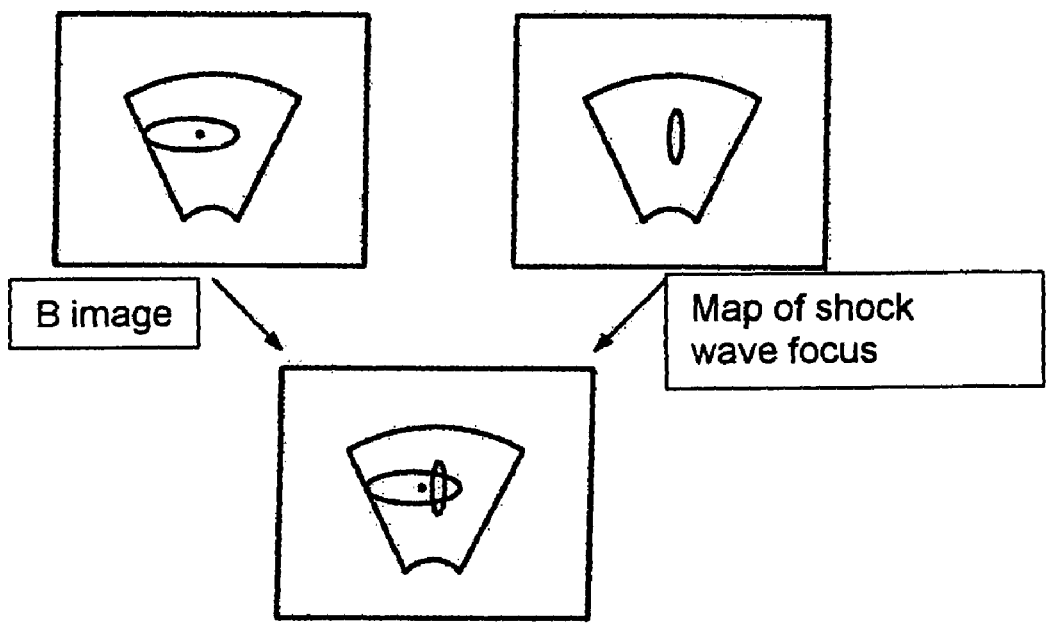
FIG. 5 shows a schematic diagram of the overlapping of the various items of image information.

FIG. 5 shows a normal B image on the top left, showing an organ with a concrement in diagrammatic form. The organ is ellipsoid and the concrement is shown in it by a black dot.

The image of the shock wave focus as it is obtained with the above-mentioned device is shown in FIG. 5 on the top right. By superimposing or overlapping the two images which have been obtained with the same ultrasound transducer, it is thus possible to achieve a correlation not susceptible to error between the concrement and the shock wave focus.

Figure 6A:
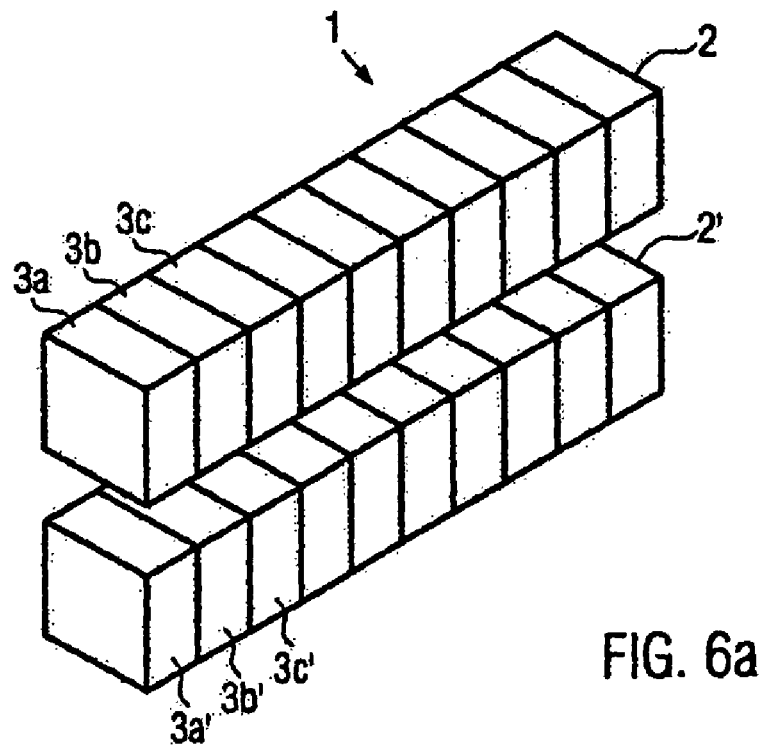
FIG. 6 shows a schematic diagram of various ultrasound units.

FIG. 6a shows an ultrasound unit 1 which comprises two transducers 2, 2'. Each transducer 2, 2' is made up of transducer elements 3a, 3b, 3c, . . . , 3a', 3b', 3c' Each of these transducer elements 3a, 3b, 3c, . . . , 3a', 3b', 3c', . . . is, for example, a piezoelectric element. If necessary, the transducer elements 2 are of a different size to the transducer elements 2'. The transducer elements of transducer 2 have a different frequency characteristic than the transducer elements of the transducer 2'. In this way, a transducer can be used for producing the normal ultrasound images (such as B images), while the other is used for the reception of the reflected and/or scattered shock wave components. The two transducers can be separately optimized for the respective requirements with their frequency characteristics (e.g. given through the resonance frequency and resonance width).

Figure 6B:
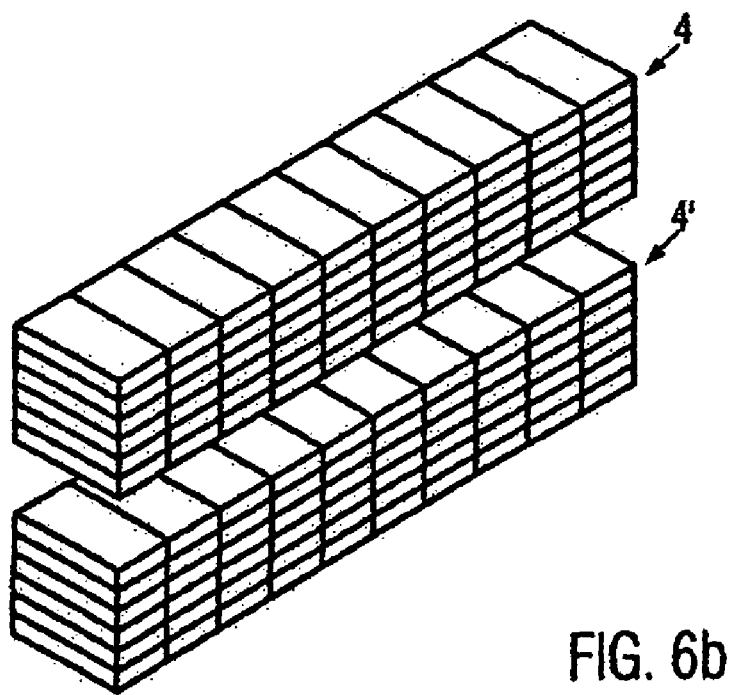

While FIG. 6a shows the case of two 1-dimensional transducers 2, 2', FIG. 6b shows the case of two 2-dimensional array-type transducers 4, 4'.

The direction of radiation of the transducers in FIGS. 6 and 7 is to the right in each case. The incoming acoustic signals to be received also come from the right.

Figure 7A:
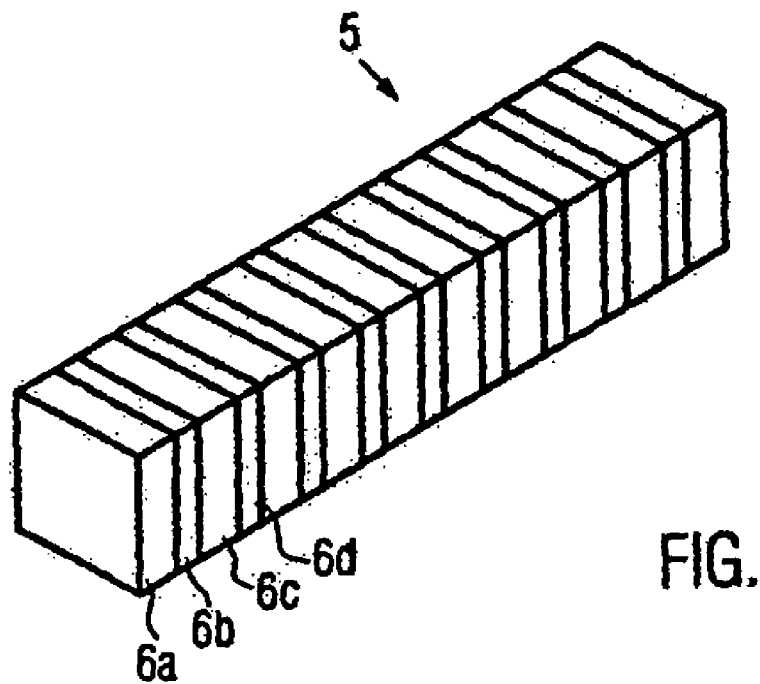
FIG. 7 shows a schematic diagram of other ultrasound units.

FIG. 7a shows a transducer 5 with two different types of transducer elements 6a, 6b, 6c, 6d. The transducer elements 6a and 6c are larger than the transducer elements 6b and 6d. The different transducer elements do not need, however, to be of different sizes. For example, they may vary in their frequency characteristics instead, or additionally. The elements 6a, 6c can be used for the production of normal ultrasound images (such as B images), while the others 6b, 6d are used to receive the reflected and/or scattered shock wave components.

Figure 7B:
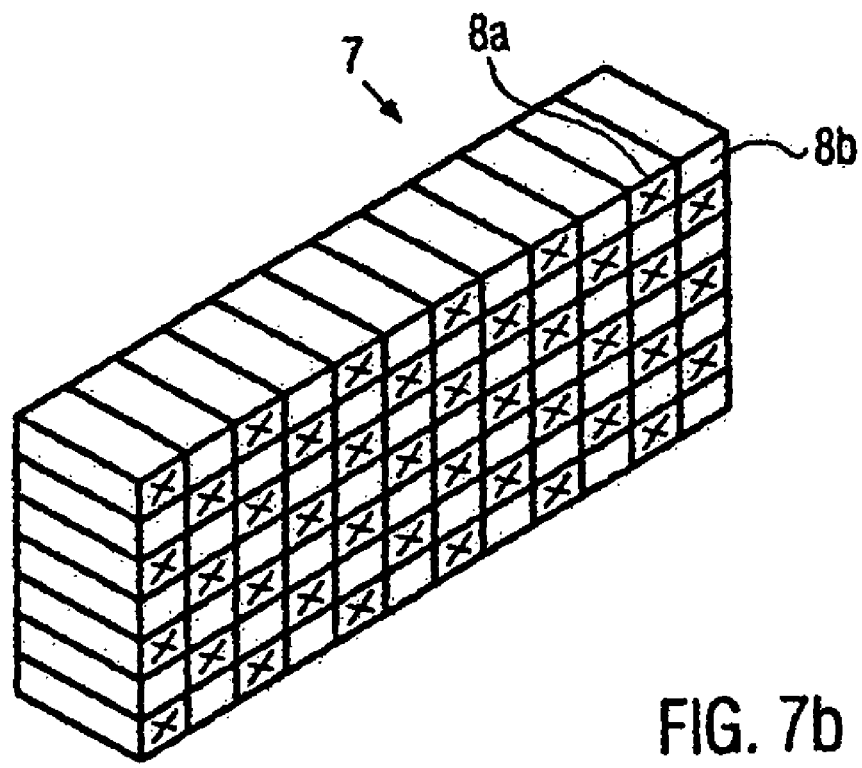

FIG. 7b shows the case of a 2-dimensional transducer 7 where transducer elements of different types 8a, 8b are arranged next to each other, here specifically in the form of a check board. The one transducer elements 8a are marked with a cross, to distinguish them, while the others 8b are not marked.

With the method, the transducer in FIG. 2 emits and receives ultrasound. The received ultrasound is converted by the transducer into an electrical signal. A control unit controls a switch in such a way that the signal is taken, after filtering, pre-amplification and digitization, to a B image processor. This then evaluates the images in the normal way and takes them to a display so that a map of the concrement is obtained using the transducer.

For emission focusing, a transmit beam former is used which is controlled by a control unit. The control unit then triggers the emission of a shock wave from the shock wave source. The emission of ultrasound with the transmit beam former and the transducer is thus interrupted. Furthermore, the control unit forwards the signals from the transducer received from this time to the shock wave signal processor. The emitted shock wave is reflected and scattered in the medium to which it was sent. These reflected and/or scattered components are received by the transducer, converted into electrical signals and forwarded via the filter 2, a pre-amplifier and an A/D converter to the shock wave signal processor. As soon as these signals have died off or after a preset time, the control unit sets the transmit beam former and the transducer back to normal image production (B image) and the signals from the A/D converter are taken to the B image processor so that ultrasound images continue to be obtained.

If different transducers or transducer elements are used for B image production and signal production for the shock wave signal processor, the switch which is controlled by the control unit is no longer necessary. Both types of image production can then be carried out at the same time next to each other. This also means that the B image production does not need to be interrupted during shock wave emission. However, if different transducer elements of a transducer are used the signals for the B image processor and the shock wave signal processor should be suitably divided, with either the digitized data or the analog signals being divided. Correspondingly separated wiring of the different types of transducer elements can also be implemented here.

By superimposing or overlapping the image information that has been obtained with the B image processor and the shock wave signal processor (see FIG. 2) (which can be done, for example, by simply adding the image signals), these can be shown on a single screen in superposition, as shown in FIG. 5. The different items of screen information can be advantageously set separately in terms of brightness and other image parameters, so that none of the items of image information completely eclipses the others. Presentation in different colours is also possible. The superimposing the image information means that the location of the shock wave focus and the concrement can be seen immediately, so that the shock wave source or shock wave focus can be adjusted or tuned.

Image production through the emission and reception of ultrasound and through the reception of reflected or scattered components of the shock wave can be carried out several times one after another. Typically, during lithotripsy treatment, 1000 to 2000 shock waves are emitted. For each shock wave, the device switches back and forth once between the different types of image production unless both image productions can be operated at the same time.

The ultrasound unit can in principle be arranged in any way in relation to the shock wave source. However, an arrangement is advantageous in which the ultrasound takes the same pathway as the shock wave source so that the medium through which the shock wave runs can be displayed itself with the ultrasound. This can be achieved, for example, by positioning the ultrasound unit centrally in front of the shock wave source.

This is advantageous, for example, for the detection of cavitation blisters, etc., which have a negative effect on the shock wave.

The invention claimed is:

1. A shock wave therapy device, comprising:
   a shock wave source that emits a shock wave;
   an ultrasound unit that emits an ultrasound and that receives a plurality of reflections of the emitted ultrasound, the ultrasound unit further receiving at least one of reflected and scattered components of the emitted shock wave;
   a B-image processor that receives from the ultrasound unit signals corresponding to the plurality of reflections of the emitted ultrasound and that processes the received signals corresponding to the plurality of reflections of the emitted ultrasound to produce ultrasound image information; and
   a shock wave signal processor that receives from the ultrasound unit signals resulting from the at least one of reflected and scattered components of the emitted shock wave and that processes the received signals resulting from the at least one of reflected and scattered components of the emitted shock wave to produce shock wave image information.

2. The shock wave therapy device of claim 1, wherein the shock wave signal processor produces shock wave image information for a shock wave focus.

3. The shock wave therapy device of claim 1, wherein the ultrasound unit comprises one or more transducers that each comprise a plurality of transducer elements.

4. The shock wave therapy device of claim 3, wherein the plurality of transducer elements comprise piezoelectric elements.

5. The shock wave therapy device of claim 3, wherein the plurality of transducer elements are arranged as one of:
   a straight line of transducer elements on a flat surface;
   a straight line of transducer elements on a curved surface;
   a curved line of transducer elements on a flat surface; and
   a curved line of transducer elements on a curved surface.

6. The shock wave therapy device of claim 3, wherein the one or more transducers comprise different frequency characteristics.

7. The shock wave therapy device of claim 3, wherein the plurality of transducer elements comprise different frequency characteristics.

8. The shock wave therapy device of claim 1, further comprising an electronic signal processing device comprising the B-image processor and the shock wave signal processor that processes a plurality of signals received by the ultrasound unit, the plurality of signals comprising the reflections of the emitted ultrasound and at least one of the reflected and scattered components of the emitted shock wave.

9. The shock wave therapy device of claim 8, wherein the electronic signal processing device further provides at least one of radiation focusing and reception focusing.

10. The shock wave therapy device of claim 1, wherein the emission and reception of the ultrasound are conducted at a different time than the reception of the reflected and scattered components of the shock wave.

11. The shock wave therapy device of claim 1, wherein the emission and reception of the ultrasound are conducted at a same time as the reception of the reflected and scattered components of the shock wave.

12. The shock wave therapy device of claim 1, wherein the ultrasound image information and the shock wave image information are used to produce a single image.

13. The shock wave therapy device of claim 1, wherein the ultrasound image information is used to produce a B image.

14. The shock wave therapy device of claim 1, further comprising a sensor that records the time of the emission of the shock wave.

15. The shock wave therapy device of claim 1, wherein the ultrasound unit receives a plurality of reflections of the emitted ultrasound with a frequency between 1 MHz and 8 MHz.

16. The shock wave therapy device of claim 3, wherein the plurality of transducer elements comprises a plurality of first transducer elements that have a maximum reception sensitivity below a specific frequency.

17. The shock wave therapy device of claim 3, wherein the plurality of transducer elements comprises a plurality of second transducer elements that have a maximum reception sensitivity above a specific frequency.

18. The shock wave therapy device of claim 15, wherein the shock wave source emits shock waves with a maximum intensity at a frequency below 1 MHz.

19. The shock wave therapy device of claim 1, wherein the shock wave source is an electromagnetic shock wave source.

20. The shock wave therapy device of claim 1, wherein the ultrasound unit is arranged centrally in front of the shock wave source.

21. A method for obtaining ultrasound image information and shock wave image information, comprising the steps of:
emitting an ultrasound from an ultrasound unit;
receiving by the ultrasound unit a plurality of reflections of the emitted ultrasound;
processing the received ultrasound reflections by a B-image processor to produce ultrasound image information;
emitting a shock wave from a shock wave source;
receiving by the ultrasound unit a plurality of reflected and scattered components of the shock wave;
processing by a shock wave signal processor the received components of the shockwave to produce shock wave image information; and
presenting the ultrasound image information and the shock wave image information on a display.

22. The method of claim 21, wherein the steps of receiving a plurality of reflected and scattered components of the shock wave and receiving a plurality of reflections of the emitted ultrasound are performed by one or more transducers of a plurality of transducer elements of the ultrasound unit.

23. The method of claim 21, further comprising the steps of:
receiving the plurality of reflected and scattered components of the shock wave for processing at a first transducer of the ultrasound unit; and
receiving the plurality of reflections of the emitted ultrasound for processing at a second transducer of the ultrasound unit.

24. The method of claim 21, wherein the steps of emitting an ultrasound and receiving a plurality of reflections of the emitted ultrasound are performed at a different time than the step of receiving a plurality of reflected and scattered components of the shock wave.

25. The method of claim 21, wherein the steps of emitting an ultrasound and receiving a plurality of reflections of the emitted ultrasound are performed at a same time as the step of receiving a plurality of reflected and scattered components of the shock wave.

26. The method of claim 21, wherein the presenting step comprises producing a single image from the ultrasound image information and the shock wave image information.

27. The method of claim 21, wherein the presenting step comprises producing a B image from the ultrasound image information.

28. A shock wave therapy device, comprising:
a shock wave source that emits a shock wave;
an ultrasound unit that emits ultrasound and that comprises at least one transducer, the at least one transducer of the ultrasound unit receiving reflections of the emitted ultrasound and converting the received reflections of the ultrasound into electrical ultrasound signals, and the at least one transducer of the ultrasound unit receiving reflected or scattered components of the emitted shock wave and converting the received components of the emitted shock wave into electrical shock wave signals;
a display;
an ultrasound image processor that processes the electrical ultrasound signals to create an ultrasound image that is displayed on the display; and
a shock wave image processor that processes the electrical shock wave signals to create a shock wave image that is displayed on the display.

29. The shock wave therapy device of claim 28, wherein the shock wave image displayed on the display represents a focus of the shock wave.

30. The shock wave therapy device of claim 28, wherein the at least one transducer of the ultrasound unit simultaneously receives the ultrasound reflections and the shock wave components.

31. The shock wave therapy device of claim 28, wherein the at least one transducer comprises a plurality of transducer elements.

32. The shock wave therapy device of claim 31, wherein a portion of the transducer elements receives the ultrasound reflections, and wherein another portion of the transducer elements receives the shock wave components.

33. The shock wave therapy device of claim 31, wherein the transducer elements comprise different frequency characteristics.

34. The shock wave therapy device of claim 28, wherein the at least one transducer of the ultrasound unit receives the ultrasound reflections and the shock wave components at different times.

35. The shock wave therapy device of claim 28, further comprising a controller that interrupts the ultrasound emissions from the ultrasound unit prior to emission of the shock wave from the shock wave source and that resumes ultrasound emissions from the ultrasound unit after emission of the shock wave from the shock wave source.

36. The shock wave therapy device of claim 28, wherein the emission and reception of the ultrasound reflections by the ultrasound unit are conducted simultaneously with the reception of the components of the shock wave by the ultrasound unit.

37. The shock wave therapy device of claim 28, wherein the at least one transducer of the ultrasound unit receives reflections of the emitted ultrasound having a frequency between 1 MHz and 8 MHz, and wherein the shock wave source emits shock waves having a maximum intensity at a frequency below 1 MHz.

* * * * *